(12) United States Patent
EL-Naggar et al.

(10) Patent No.: US 6,908,907 B2
(45) Date of Patent: Jun. 21, 2005

(54) PREVENTION AND TREATMENT OF TUMOR GROWTH, METASTASIS, AND THROMBOEMBOLIC COMPLICATIONS IN CANCER PATIENTS

(76) Inventors: Mawaheb M. EL-Naggar, 7 Linden Cir., Lincoln Univ., PA (US) 19352; Shaker A. Mousa, 7 Linden Cir., Lincoln Univ., PA (US) 19352

( * ) Notice: Subject to any disclaimer, the term of this patent is extended or adjusted under 35 U.S.C. 154(b) by 27 days.

(21) Appl. No.: 10/125,882

(22) Filed: Apr. 22, 2002

(65) Prior Publication Data

US 2004/0214751 A1 Oct. 28, 2004

(51) Int. Cl.$^7$ .................. A61K 31/727; A61K 3/422
(52) U.S. Cl. .................. 514/56; 514/378; 514/380
(58) Field of Search ............... 514/56, 380, 378

(56) References Cited

U.S. PATENT DOCUMENTS

| | | | | |
|---|---|---|---|---|
| 4,401,662 A | * | 8/1983 | Lormeau et al. | 514/56 |
| 4,971,956 A | * | 11/1990 | Suzuki et al. | 514/55 |
| 5,229,504 A | * | 7/1993 | Hayashi | 536/20 |
| 6,057,291 A | * | 5/2000 | Hancock et al. | 514/12 |
| 6,306,886 B1 | * | 10/2001 | Maurin et al. | 514/378 |
| 6,322,550 B2 | * | 11/2001 | Iga et al. | 604/501 |
| 6,346,517 B1 | * | 2/2002 | Wong et al. | 514/56 |
| 6,518,244 B2 | * | 2/2003 | Cardin et al. | 514/11 |

OTHER PUBLICATIONS

Loreto, M. F., "Coagulation and cancer" (2000) Patholog. Oncolog. Res. vol 6, no 4, pp. 301–312.*

Smorenburg, S. M. "The complex effects of heparins on cancer . . . " (2001) Pharmalog. Rev. vol 53, no 1, pp. 93–105.*

* cited by examiner

Primary Examiner—James O. Wilson
Assistant Examiner—Leigh C. Maier
(74) Attorney, Agent, or Firm—Schmeiser, Olsen & Watts

(57) ABSTRACT

This invention provides for the prevention and treatment of tumor growth, metastasis, and cancer-mediated thrombosis through the administration, in combination, of a short or long acting GPIIb/IIIa antagonist (A) and anticoagulant (B) that might include the following: UFH or low molecular weight heparin, (LMWH), ultra LMWH, pentasaccharide or direct anti-Xa or direct anti-IX/IXa, direct anti-IIa (thrombin) or tissue factor pathway inhibitor (TFPI) by any means that produces contact of the agents with their site of action wherein at least one of the components of each of these combinations is given in reduced amount. This combined formulation could be used as a stand-alone regimen or in conjunction with other therapies (chemotherapy, radiotherapy, angiogenesis inhibitors, . . . ), and pre- & post-tumor surgery in the prevention and treatment of cancer associated metastasis, angiogenesis, tumor growth, and thrombosis.

17 Claims, 1 Drawing Sheet

PREVENTION AND TREATMENT OF TUMOR GROWTH, METASTASIS, AND THROMBOEMBOLIC COMPLICATIONS IN CANCER PATIENTS

FIELD OF THE INVENTION

This invention relates to the prevention and treatment of tumor growth, metastasis, and cancer associated thromboembolic disorders, and more particularly to such treatment by the administration of a lyophilized formulation of an antiplatelet such as the platelet GPIIb/IIIa antagonist, and an anticoagulant such as unfractinoated heparin (UFH), low molecular weight heparin (LMWH), ultra LMWH, pentasaccharide, direct anti-Xa, anti-IX/IXa, direct anti-IIa (thrombin), anti-VIIa, anti-tissue factor or recombinant tissue factor pathway inhibitor (r-TFPI) at sub-therapeutic levels. This combined formulation could be used as a stand-alone regimen or in conjunction with other therapies (chemotherapy, radiotherapy, angiogenesis inhibitors, . . . ), and pre- & post-tumor surgery in the prevention and treatment of cancer associated metastasis, angiogenesis, tumor growth, and thrombosis.

BACKGROUND OF THE INVENTION

Many cancer patients reportedly have hyper-coaguable state, with recurrent thrombosis due to the impact of cancer cells and chemotherapy on the activation of the coagulation cascade. Studies have demonstrated that UFH or LMWH interferes with various processes involved in tumor growth and metastasis. These processes might include fibrin formation, binding of heparin to angiogenic growth factors such as basic fibroblast growth factor (FGF2) and vascular endothelial growth factor (VEGF), modulation of tissue factor (TF), release of endogenous TFPI, and other mechanisms. Clinical trials have indicated a clinically relevant effect of LMWH, as compared to UFH on the survival of cancer patients with deep vein thrombosis. Recent studies defined the role of the LMWH, anti-factor VIIa and r-TFPI in the modulation of angiogenesis, tumor growth, and tumor metastasis (Mousa and. Fareed, Current Opinion In investigational Drugs, 2:1077–1080, 2001; Mousa, Seminar Thrombosis & Haemostasis, 28:45–52, 2002).

Heparin and LMWH: Despite the research and development efforts in newer anticoagulants, UFH and LMWH will continue to play a pivotal role in the management of thrombotic disorders. While bleeding and heparin-induced thrombocytopenia represent major side effects of this drug, it has remained the anticoagulant of choice for the prophylaxis and treatment of arterial and venous thrombotic disorders, surgical anticoagulation and interventional usage. It is the understanding of the structure of heparin which led to the development of LMWHs, synthetic heparinomimetics, antithrombin and anti-Xa agents (Weitz, N Engl J Med, 337:688–698, 1997; Aguilar and Gldhaber, Chest, 115:1418–1423, 1999; Linhardt and Gunay, Seminar Thromb Haemost., 25:5–16, 1999; Mousa and Fareed, Exp Opin Invest Drugs, 10:157–162, 2000).

As heparin was discovered over a half of a century ago, our knowledge of the chemical structure and molecular interactions of this fascinating polycomponent was limited at the early stages of its development. Through the efforts of major multidisciplinary group of researchers and clinicians, it is now well recognized that heparin has multiple sites of actions and can be used in multiple indications. It is not too distant in the future to witness the impact of these drugs on the management of various diseases.

Tinzaparin sodium is a low molecular weight heparin produced by controlled enzymatic depolymerization of conventional, unfractionated porcine heparin (Linhardt and Gunay, Seminar Thromb Haemost., 25:5–16, 1999; Nader et al., Seminar Thromb Haemost., 25:63–72, 1999; Mousa, Thromb Haemost.,26:39–46, 2000). In clinical trials, Tinzaparin is more effective than unfractionated heparin as treatment for deep vein thrombosis (DVT), is effective in the treatment of pulmonary embolism and the prevention of DVT in abdominal surgery patients, and is superior to Warfarin as thromboembolism prophylaxis in subjects undergoing orthopedic joint (hip or knee) replacement surgery (Hull et al, New Engl J Med, 326:975–982, 1992; Simonneau et al., N Engl J Med 337, 663–669, 1997; Hull et al., N Engl J Med., 329:1370–1376, 1993; Leizorovicz et al., Br J Surgery, 78:412–416, 1991).

Anti-Xa activity has served as the primary biomarker for assessing the exposure of Tinzaparin and other low molecular weight heparin. It is used to define the in vitro potency and to monitor therapeutic response (Troy et al., Thromb Haemost 78:871–875, 1997). Given that LMWHs are polycomponent moieties with multiple biological actions each with distinct time courses, the true pharmacokinetic behavior of these agents cannot be assessed with assays developed for a single pharmacological activity. The absolute bioavailability is approximately 90% based on anti-Xa activity (Pederson et al., Thromb Res., 61:477–487, 1991) and 93% based on plasma TFPI.

Recent clinical trials in which LMWHs with distinct in vitro potency (anti-Xa: anti-IIa ratio) and ex vivo anti-Xa and anti-IIa activities were tested in DVT patients following hip replacement found no difference in efficacy or safety measures as compared to UFH (Bara et al., Br J Hematol., 104:23–240, 1999) despite distinct differences in biomarker activity profiles. However, anti-Xa activity is sensitive as an indicator of molecular weight distribution differences with various heparin fractions. LMWHs vary in their affinity for ATIII, presumably as a result of production method Brieger and Dawes, Thromb Haemost 77: 317–322, 1997). Such differences have been cited as explaining, in part, the differences in LMWH pharmacodynamics as assessed by anti-Xa activity and one reason why they cannot be used interchangeably. In contrast, TFPI, a vascular endothelial biomarker might represent a greater potential for the role of LMWH in various diseases (Mousa et al., Blood, 16 (11):59, 3929, 2000; Mousa and Mohamed, Blood, 94 (10): Suppl. 1, 22a, 82, 1999).

Thrombosis and cancer: The etiology of thrombosis in malignancy is multi-factorial, and mechanisms include release of pro-coagulants by tumor cells plus other predisposing hyper-coaguable state-mediated by chemotherapeutic and radio-therapeutic agents (Goldberg et al., Ann Intern Med 147: 251–253, 1987; Baron et al., Lancet 351: 1077–1080, 1998; Rickles and Edwards, Blood 62:14–31, 1982; Levine et al., N Engl J Med., 318: 404–407, 1998; Kakkar et al., Lancet, 346:1004–1005, 1995). Unexplained thromboembolism may be an early indicator of the presence of a malignant tumor before signs and symptoms of the tumor itself become obvious (Goldberg et al., Ann Intern Med 147: 251–253, 1987).

Haemostatic abnormalities are present in a majority of patients with metastatic cancer. These abnormalities can be categorized as 1) increased platelet aggregation and activation, 2) abnormal activation of coagulation cascade, 3) release of PAI-1, and 4) decrease hepatic synthesis of anticoagulant proteins like Protein C and antithrombin III. The abnormal activation of coagulation cascade is mediated through release of Tissue Factor, and other pro-coagulants (FIG. 1) from the plasma membrane vesicles of tumor cells (Rickles and Edwards, Blood 62:14–31, 1982; Kakkar et al., Lancet, 346:1004–1005, 1995).

Increasing evidence suggests that thrombotic episodes may also precede the diagnosis of cancer by months or years thus representing a potential marker for occult malignancy (Goldberg et al., Ann Intern Med 147: 251–253, 1987). Recently, emphasis has been given to the potential risk of cancer therapy (both surgery and chemotherapy) in enhancing the risk for thromboembolic disease (Rickles and Edwards, Blood 62:14–31, 1982; Kakkar et al., Lancet, 346:1004–1005, 1995). Post-operative deep-vein thrombosis is indeed more frequent in patients operated for malignant diseases than for other disorders. On the other hand, both chemotherapy and hormone therapy are associated with an increased thrombotic risk, which can be prevented by low-dose oral anticoagulation (Kakkar and Williamson, Haemost., 27: (Suppl. 1): 32–37, 1997). In particular, pro-coagulant activities of tumor cells have been extensively studied; one of this specific tumor pro-coagulant could represent a novel marker of malignancy.

Treatment of VTE in Cancer Patients: The management of DVT and PE in patients with cancer can be a clinical dilemma. Comorbid conditions, Warfarin failure, difficult venous access, and a high bleeding risk are some of the factors that often complicate anticoagulant therapy in these patients. In addition, the use of central venous access devices is increasing but the optimal treatment of catheter-related thrombosis remains controversial. UFH is the traditional standard for the initial treatment of VTE but LMWHs have been shown to be equally safe and effective in hemodynamically stable patients. For long-term treatment or secondary prophylaxis, vitamin K antagonists remain the mainstay treatment. However, the inconvenience and narrow therapeutic window of oral anticoagulants make extended therapy unattractive and problematic. As a result, LMWHs are being evaluated as an alternative for long-term therapy. The role of inferior vena cava filters in cancer patients remains ill defined but these devices remain the treatment of choice in patients with contraindications for anticoagulant therapy.

A growing body of evidence has provided the convincing demonstration of a strong association between cancer and venous thromboembolism (Table 1). Patients with cancer are at a remarkably higher risk of venous thromboembolism than patients free from malignant disorders during prolonged immobilization from any cause, and following surgical interventions. Standard heparin in adjusted doses or a low-molecular-weight heparin in doses commonly recommended for high risk surgical patients represent the prophylactic treatment of choice for cancer patients undergoing an extensive abdominal or pelvic intervention. In cancer patients affected by deep-vein thrombosis, the treatment with low-molecular-weight heparin has been reported to lower mortality at a higher extent than the standard heparin therapy. Such an observation suggests that these agents might modify tumor growth progression directly or indirectly (Zacharski and Ornsteing, Thromb Haemost., 80: 10–23, 1998; Gillis et al., Eur J Haematol., 54: 59–60, 1995).

Recent studies provided convincing evidence for increased incidences of newly diagnosed malignancy among patients with unexplained venous thromboembolism (VTE) during the first 6–12 months after the thromboembolic event (Zacharski and Ornsteing, Thromb Haemost., 80: 10–23, 1998; Gillis et al., Eur J Haematol., 54: 59–60, 1995; Howard, Lancet, 1:650–655, 1906; Dvorak, Human Pathol., 18: 275–284, 1987). Table 1 list tumor types associated with VTE and FIG. 2 illustrate the positive feedback loop between tumor and clot in magnifying each other.

Tumor-fibrin is a consistent feature of tumor stroma and is deposited shortly after tumor cell inoculation (Dvorak et al., Cancer Metastasis rev., 2: 41–73, 1983). Since there are several ways in which fibrin may be beneficial to tumor growth, it is possible that the ability of normal or malignant tissue to generate fibrin may influence metastasis. Different normal tissues and tumor cells possess a pro-coagulant activity that is due to a complex of tissue factor and factor VII (Falanga, Haemost., 28: 50–60, 1998).

Angiogenesis: Angiogenesis is a process that is dependent upon coordinate production of angiogenesis stimulatory and inhibitory (angiostatic) molecules and any imbalance in this regulatory circuit might lead to the development of a number of angiogenesis-mediated diseases. Angiogenesis is a multistep process including: activation, adhesion, migration, proliferation and transmigration of endothelial cells across cell matrices to or form new capillaries and from existing vessels. Angiogenesis is a process involved in the formation of new vessels by sprouting from preexisting vessels. In contrast, vessel rudiments may organize in place a process termed vasculogenesis. Endothelial heterogeneity and organ specificity might contribute to differences in the response to different anti-angiogenic mechanisms (cultured EC vs. microvascular EC isolated from different tissues). Under normal physiological conditions, in mature organism endothelial cell turnover or angiogenesis is extremely slow (months to years). However, angiogenesis can be activated for a limited time in certain situations such as wound healing and ovulation. In certain pathological states, such as human metastasis and ocular neovascularization disorders including diabetic retinopathy and age-related macular degeneration there is excessive and sustained angiogenesis. Hence understanding the mechanisms involved in the regulation of angiogenesis could have a major impact in the prevention and treatment of pathological angiogenesis processes. Additionally, endothelial cells play a major role in the modeling of blood vessels. The interplay of growth factors, cell adhesion molecules and specific signal transduction pathways either in the maintenance of the quiescent state or in the reactivation of endothelial is critical in physiological and pathological angiogenesis processes. A combined defect in the overproduction of positive regulators of angiogenesis and a deficiency in endogenous angiostatic mediators are a feature documented in tumor angiogenesis, psoriasis, RA and other neovascularization-mediated disorders. Hence understanding the mechanisms involved in the regulation of angiogenesis could have a major impact in the treatment of pathological angiogenesis (Mousa, In angiogenesis inhibitors and stimulators, Ed. By Mousa, Landes Co., Tex., chapter 1:1–12, 2000).

Activation of coagulation and angiogenesis in cancer: Tissue factor has been implicated in the upregulation of pro-angiogenic factors such as VEGF by tumor cells. This is due to a complex interaction between tumor cells, macrophage, and endothelial cells leading to TF expression, fibrin formation, and tumor angiogenesis (Bell, Semin Thromb Haemost., 22:459–478, 1996; Ruf et al., Curr Opin Haematol., 3:379–384, 1996).

Anticoagulants in the modulation of angiogenesis: The effects of LMWH Tinzaparin, Warfarin, anti-VIIa and r-TFPI on the modulation of angiogenesis related processes including in vitro endothelial tube formation and in vivo angiogenesis-mediated by angiogenic factors and cancer cells were demonstrated. The in vivo effects of those different anti-coagulants on angiogenesis in the chick chorioallantoic membrane (CAM) model were determined. Twenty-four hours after stimulating angiogenesis on the CAM with FGF2, lipopolysaccharide (LPS) or colon carcinoma (HCT-116), Tinzaparin, Warfarin, anti-VIIa or r-TFPI were directly applied to the growth factor saturated filter disk or were injected intravenously into the embryonic circulation. Data demonstrated significant and comparable inhibitory effects of the LMWH Tinzaparin, anti-VIIa or r-TFPI in a concentration-dependent manner on endothelial cell tube formation. Both Tinzaparin, Warfarin, anti-VIIa and r-TFPI blocked FGF2-induced angiogenesis in the CAM model by 80–100%. Additionally, a significant inhibition of colon or lung carcinoma-induced angiogenesis, tumor growth and regression was demonstrated with Tinzaparin, anti-VIIa and r-TFPI. These studies demonstrated a significant role for Tinzaparin, Warfarin, anti-VIIa and Tinzaparin releasable TFPI on the regulation of angiogenesis and tumor growth (Mousa, Semin Thromb Haemost., 28: 45–52, 2002). Thus, modulation of tissue factor/VIIa non-coagulant activities by those different agents might be a useful therapeutic for the inhibition of angiogenesis associated with human tumor growth and inflammatory diseases.

See Table 2 for diseases associated with pathological angiogenesis.

LMWH, TFPI and Tumor Dissemination: The significance of Tissue factor (TF) in cancer biology is suggested by studies reporting its involvement in metastasis and angiogenesis. Tinzaparin is a low molecular weight heparin that is produced by heparinase depolymerization of unfractionated heparin allowing for its relatively high sulfate to carboxylate ratio. Beyond its potent plasmatic effects on ATIII-dependent coagulation factors, Tinzaparin is a very effective LMWH in causing the release of TFPI from the endothelial cells, the natural inhibitor of tissue factor pro-coagulant and non-coagulant effects. The present study was undertaken to investigate the effect of the LMWH, Tinzaparin as well as recombinant TFPI on experimental lung metastasis. Using the B16 melanoma injectable model of metastasis, we found that subcutaneous injection of Tinzaparin (10 mg/kg) 4 hrs before intravenous injection of $2.5 \times 10^5$ melanoma cells, reduced lung tumor formation in experimental mice by 89% (31±23 Vs 3±2, P<0.001). In a second experimental group, in addition to the initial (pre-tumor cell) dose, subcutaneous Tinzaparin (10 mg/kg) was administered daily for 14 days at which time lung seeding was assessed. In the latter group, lung tumor formation was reduced by 96% (P<0.001). No bleeding problems were observed in any of the heparinized animals. In order to determine the anticoagulant activity of Tinzaparin, 4 hrs after a single subcutaneous dose, whole blood re-calcification was measured using a Sonoclot Analyzer. Tinzaparin (10 mg/kg S.C.) prolonged the clotting time 4 fold. Furthermore, measuring the platelet count (a sensitive marker of intravascular coagulation) before and 15 minutes determined the effect of Tinzaparin on tumor cell-induced clotting activation in vivo after tumor cell injection in control and Tinzaparin-treated animals. Following I.V. injection of $2 \times 10^6$ tumor cells, a rapid and significant fall in platelet count was observed (from $939 \pm 37 \times 10^6$/ml to $498 \pm 94 \times 10^6$/ml, P<0.01). In Tinzaparin-treated animals, a significant reversal to normal platelet count was achieved ($921 \pm 104 \times 10^6$/ml). Intravenous injection of TFPI (700 ng) 5 minutes prior to tumor cell injection, also reduced B16 lung metastasis (85%, P<0.01) and abolished tumor cell induced thrombocytopenia. Results support the potential role of the LMWH Tinzaparin and its releasable TFPI in tumor metastasis (Amirkhosravi, et al., Thromb Haemost.,P1409, 2001; Mousa, Semin Thromb Haemost., 28:45–52,2002) .Similar data were demonstrated with platelet GPIIb/IIIa antagonists in the same models, with 75–85% inhibition of tumor metastasis. However neither LMWH nor GPIIb/IIIa antagonist fully prevent tumor metastasis.

Haemostasis & Tumor Dissemination: Platelet and fibrin are key catalysts for tumor adhesion, survival, and metastasis. Tumor cell metastasis and thrombosis are the major causes of death in cancer patients (Frances, Med Lab Sci., 46: 331–346, 1989; Dvorak, Hum Pathol., 18: 275–284, 1987).

Tumors are dynamic, complex, living tissues undergoing the varied processes of tissue growth under the guidance of aberrant malignant cells. Cytotoxic anticancer therapies have focused solely on the eradication of the malignant cell, which is an absolute necessity; however, even the most heroic therapeutic strategies rarely achieve cure of many tumor types (Brewer, Nature Biotechnology,17:963–968, 1999; Paku, Pathol Oncol. Res., 4: 62–75, 1998). The recognition that the growth processes of tumors are normal processes, that the invasion processes of tumors are normal processes and that it is in appropriate activation of the processes that comprises the morbidity of malignant disease allows the elucidation of a broad spectrum of new therapeutic targets in cancer. The integration of anti-angiogenic agents into existing cancer chemotherapy regimens might lead to improved efficacy and safety for many standard catatonic therapies.

The need for an anticoagulant with standard anti-angiogenesis agent might be essential since some of these anti-angiogenesis agents increase the incidence of venous thrombosis (Osman et al., N. Engl J Med., 344:1951–1952, 2001). Hence LMWH or UFH could be a better avenue in inhibiting angiogenesis and countering any increased incidences of venous thrombosis.

Antiplatelets: Platelet GPIIb/IIIa Antagonist:

The final common step in platelet aggregation, regardless of the stimulus, involves the interaction of adhesive proteins such as fibrinogen and vWf with the platelet membrane GPIIb/IIIa (Pytela et al., Science 231:1559–1562, 1986; Philips et al., Cell 65:359–362, 1991). It is now well established that the binding of fibrinogen to the GPIIb/IIIa receptor on activated platelets is considered as the final common pathway of platelet aggregation (Mousa, Drug discovery today 4: 552–561, 1999; Mousa and Bennett, Drugs of the Future 21: 1141–1154, 1996; Bennett and Mousa, Thrombosis & Haemostasis, 85:1–6, 2001).

Thus, blockade of fibrinogen binding to the GPIIb/IIIa receptor on activated platelet should inhibit platelet aggregation induced by all agonists. Peptide, peptidomimetic and non-peptide GPIIb/IIIa antagonists have been developed, and their anti-thrombotic effects have been well demonstrated (Mousa, Drug discovery today 4: 552–561, 1999; Mousa and Bennett,. Drugs of the Future 21: 1141–1154, 1996; The EPIC Investigators, N Engl J Med., 330: 956–961, 1994; Mousa and Topol, Current review of Interventional Cardiology, $3^{rd}$ edition, Current Medicine, 13: 114–129, 1997). Clinical studies with orally active GPIIb/IIIa antagonists including Xemilofiban, Orbofiban, Sibrafiban, Lotrafiban, and LeFradafiban demonstrated variable oral antiplatelet activity in man upon their administration (Mousa, Drug discovery today 4: 552–561, 1999; Simpfendorfer et al., Circulation 96: 76–81, 1997). In contrast to the success of IV GPIIb/IIIa antagonists, recent clinical trials demonstrated lack of clinical benefit for the oral delivery of GPIIb/IIIa antagonists. Additionally, a second generation oral GPIIb/IIIa antagonists with tight binding to GPIIb/IIIa receptors along with slow dissociation rate such as Roxifiban (Mousa and Bennett, Drugs of the Future 21: 1141–1154, 1996; Mousa et al., Coronary Artery Disease 7: 767–774, 1996; Mousa et al., J Pharmacol Exp Thera., 286:1277–1284,1998) might provide improved pharmacodynamic were discontinued in light of the failure of the first generation oral agents (Simpfendorfer et al., Circulation 96: 76–81, 1997; Muller et al., Circulation 96: 1130–1138, 1997; Cannon et al., Circulation 97: 340–349, 1998; Cannon et al., Circulation 102: 149–156, 2000). The success of IV GPIIb/IIIa antagonists might be dependent on the use of an anticoagulant such as heparin, which was not included in the oral formulation.

Anticoagulants: Heparin and LMWH:

Both UFH and LMWH are polyanionic glycosaminoglycan (GAG). Compared to UFH, LMWHs exhibit improved subcutaneous (SC) bioavailability; lower protein binding; longer half-life; variable number of antithrombin III binding sites; variable glycosaminoglycan contents; variable antiserine protease activities (anti-Xa, anti-IIa); variable potency in releasing TPFPI (Young et al., Thromb Haemost 71: 300–304, 1994; Frydman, Haemost 26: 24–38, 1996; Fareed et al., Am J Cardiol 82: 3L–10L, 1988). For these reasons, over the last decade LMWHs have increasingly replaced UFH in the prevention and treatment of venous thromboembolic disorders (VTE) because of its pharmacoeconomic advantages over UFH (Hull et al., Thromb Haemost 24: 21–31, 1998; Hull et al., N Engl. J Med. 329: 1370–1376, 1993; Levine et al., N Engl. J Med. 334: 677–681, 1996; Hirsh, Semin Hematol., 34: 20–25, 1999; Simonneau et al., N Engl. J Med. 337: 663–669, 1997). Randomized clinical trials have demonstrated that individual LMWHs used at optimized dosages are at least as effective and probably safer than UFH. The convenient once- or twice daily SC dosing regimen without the need for monitoring has encouraged the wide use of LMWHs. It is well established that different LMWHs vary in their physical and chemical properties due to the differences in their methods of manufacturing. These differences translate into differences in their pharmacodynamic and pharmacokinetic characteristics (Fareed et al., Ann N.Y. Acad Sci. 556: 333–353, 1989). The World Health Organization (WHO) and United States Food and drug administration (US-FDA) regard LMWHs as individual drugs that cannot be used interchangeably (Fareed et al., Ann NY Acad Sci. 556: 333–353, 1989; Simonneau et al., N Engl. J Med. 337: 663–669,1997).

Other Anticoagulant Mechanisms Beyond Heparin:

Recently a synthetic pentasaccharide (indirect anti-Xa) was developed for the prevention and treatment of venous thromboembolic disorders and certain settings of arterial thrombosis (Hirsh and Weitz, Lancet, 93:203–241, 1999). Additionally, various direct anti-Xa were synthesized and advanced to clinical development (Phase I–II) for the prevention and treatment of venous thromboembolic disorders and certain settings of arterial thrombosis (Hirsh and Weitz, Lancet, 93:203–241, 1999; Nagahara et al., Drugs of the Future, 20: 564–566, 1995; Pinto et al., 44: 566–578,2001; Pruitt et al., Biorg Med Chem Lett, 10: 685–689, 2000; Quan et al., J Med Chem 42: 2752–2759, 1999; Sato et al., Eur J Pharmacol, 347: 231–236, 1998; Wong et al, J Pharmacol Exp Thera, 292: 351–357, 2000). A direct anti-IIa (thrombin) such as Xemilegtran is in Phase II–III of clinical development in venous and certain settings of arterial thrombosis (Hirsh and Weitz, Lancet, 93:203–241, 1999; Fareed et al., Current Opinion in Cardiovascular, pulmonary and renal investigational drugs, 1:40–55, 1999). Additionally, a number of anti-VIIa and anti-tissue factor are in pre-clinical and early stage of clinical development. Furthermore recombinant tissue factor pathway inhibitor (r-TFPI) is under preclinical and clinical investigations for a number of years (Kaiser et al, Emerging Drugs 5:73–87, 2000; G Hirsh and Weitz, Lancet, 93:203–241, 1999; Bajaj and Bajaj, Thromb Haemost, 78: 471–477, 1997; Roque et al, J Am Coll Cardiol, 36: 2303–2310, 2000).

In all of IV GPIIb/IIIa antagonist trials in arterial coronary intervention, the GPIIb/IIIa antagonists and UFH were given by IV bolus followed by IV infusion as a separate product)

Low molecular weight heparins are obtained from standard, unfractionated heparin, are as effective as standard, unfractionated heparin for prophylaxis and treatment of venous thromboembolism and have fewer side effects. The current available low molecular weight heparins include, for example, tinzaparin, certoparin, parnaparin, nadroparin, ardeparin, enoxaparin, reviparin, dalteparin and fraxiparin.

SUMMARY OF THE INVENTION

One object of the present invention is to provide a method of treating and preventing cancer associated tumor growth, metastasis, and thrombosis in a mammal comprising: administering the combination in a therapeutically effective amount of (i) a GPIIb/IIIa antagonist selected from the group consisting of Abciximab, XV454, XV459, DMP802, roxifiban (class I) as defined by Mousa et al., Athero Thromb Vasc Biol., 2000) and eptifibatide, tirofiban, DUP728, lefradafiban, sibrafiban, orbofiban, xemilofiban, lotrafiban (Class II) and an anticoagulant such as heparin selected from the group consisting of UFH or LMWH such as tinzaparin, certoparin, parnaparin, nadroparin, ardeparin, enoxaparin, reviparin, dalteparin, and fraxiparin or ultra LMWH, pentasaccharide, direct anti-Xa, direct anti-IIa (thrombin) or tissue factor pathway inhibitor (TFPI). Where in the anticoagulant is administered in a reduced to sub-therapeutic amounts or amounts that provide a synergistic to additive improvement in the therapeutic index (efficacy/safety window).

Another object of the present invention is to provide a method of preventing and treating thrombosis in cancer patients wherein the combination of (i) GPIIb/IIIa antagonists and (ii) anticoagulants listed above is administered in amounts to provide a synergistic effect on the efficacy and safety parameters by administering a lyophilized formulation containing a GPIIb/IIIa antagonist compound and sub-therapeutic amounts of an anticoagulant for in-hospital (intravenous) and out-hospital (subcutaneous or oral).

Safety Advantages for the Combination of GPIIb/IIIa Antagonists and Heparin:

It has been demonstrated that the platelet GPIIb/IIIa antagonist can effectively inhibit Heparin-induced platelet activation in plasma from heparin-induced thrombocytopenia (HIT) patients and in patients with HIT(Walenga et al.,Clin Appl Thromb Haemost 3: S53–63, 1997; Jeske et al., Thromb Res., 88:271–281, 1997; Walenga et al., Hamostaseologie, 19: 128–133, 1999; Mousa et al., J Am Coll Cardiol, 35: 1178, 317A, 2000), which would result in serious and fatal thrombotic thrombocytopenia. Furthermore, plasma from patients who developed thrombocytopenia after GPIIb/IIIa antagonist that result in increased platelet activation and secretion could be blocked by anticoagulants such as direct or indirect thrombin inhibitors. Hence the combination of both the platelet GPIIb/IIIa antagonist and anticoagulant such as UFH, LMWH, anti-Xa, anti-IX/IXa, anti-IIa, TFPI, ultra-LMWH, pentasaccharide, and other anticoagulants would result in a mutually safer formulation with less thrombocytopenia that could either the result of heparin, LMWH or the GPIIb/IIIa antagonist.

Formulation of zwitterionic GPIIb/IIIa antagonists with polyanionic heparin requires the addition of polycationic carbohydrate such as Chitosan or polycationic peptides in the presence of citric acid, sodium citrate, mannitol, and other non-active ingredients.

Formulation of zwitterionic GPIIb/IIIa antagonists with small molecules anti-Xa, anti-IIa, and other anticoagulants requires the addition of sodium caproate in the presence of citric acid, sodium citrate, mannitol, and other non-active ingredients.

DETAILED DESCRIPTION OF THE INVENTION

Figure 1:
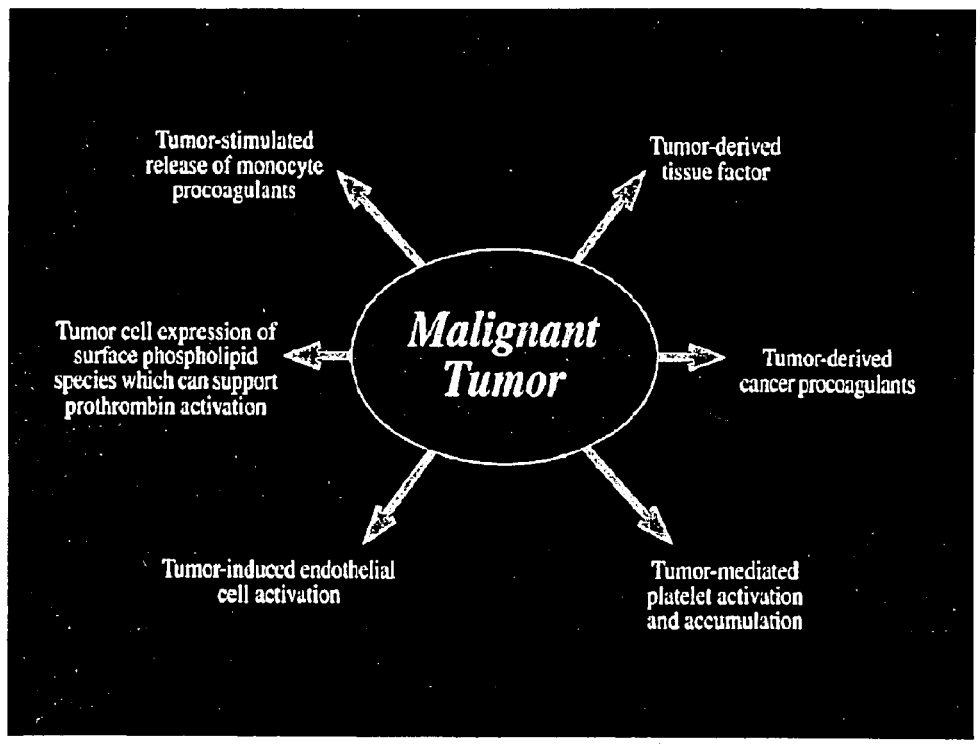
FIG. 1 illustrates the abnormal activation of coagulation cascade through release of Tissue Factor and other procoagulants from the plasma membrane vesicles of tumor cells.
Figure 2:
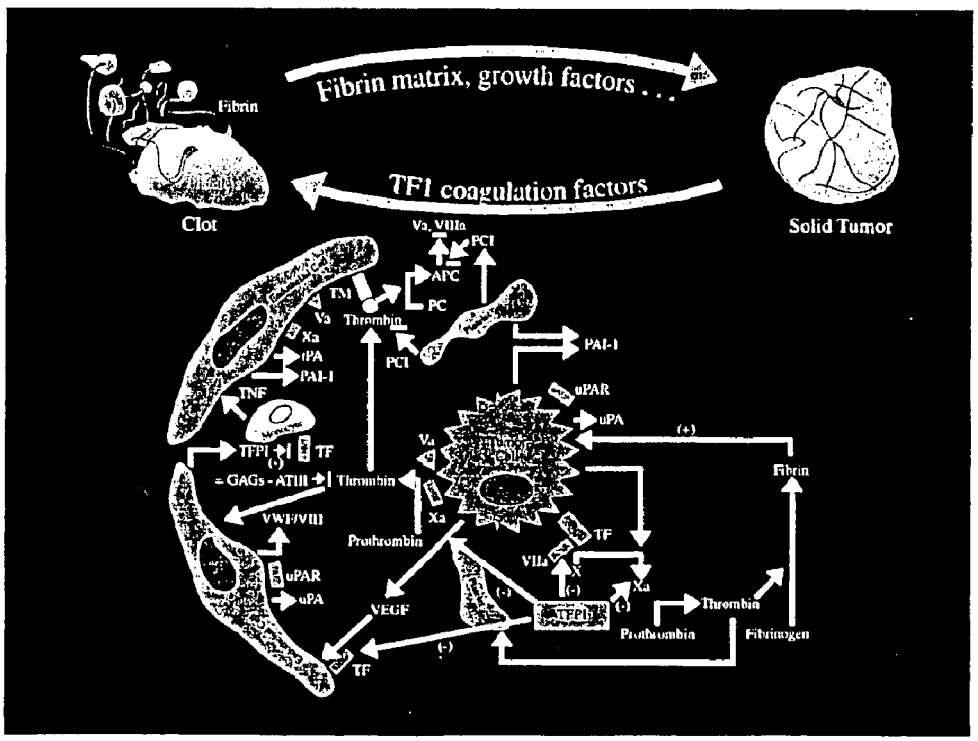
FIG. 2 illustrates the positive feedback loop between tumor and clot.

The combinations of a lyophilized or liquid formulation of a GPIIb/IIIa antagonist with an anticoagulant such as UFH, low molecular weight heparin (LMWH), ultra LMWH, pentasaccharide, direct anti-Xa, direct anti-IIa (thrombin) or tissue factor pathway inhibitor (TFPI) at reduced amounts should have a tremendous impact in cancer. The antithrombotic benefits would include the prevention and treatment of tumor growth, metastasis, and thromboembolic complications in cancer patients.

UFH and Low molecular weight heparins such as tinzaparin or other LMWH derivatives useful in the combination of the present invention are commercially available and well known in the prior art. Preferred GPIIb/IIIa antagonist compounds useful herein, as well as their preparation, are described in WO 95/14683 (the contents of which are incorporated herein by reference). Preferred compounds described therein and their preparation have the formula: Specific examples of other useful GPIIb/IIIa antagonist compounds are abciximab, eptifibatide, tirofiban, lefradafiban, sibrafiban, Orbofiban, lotrafiban, DMP728, DMP802, XV454, DMP754 (Roxifiban), XV459, and xemilofiban described in the paper of Graul et al. and Scarborough (Graul A, Martel A M and Castaner J. Drugs of the Future 22: 508–517, 1997; Scarborough R M; Eptifibatide. Drugs of the Future 23: 585–590, 1998; Mousa and Wityak., Cardiovascular Drug reviews 16: 48–61, 1998). Of these, DUP728, DMP802, XV454, XV459, DMP754 are preferred. Others will be readily apparent to those skilled in the art.

"Therapeutically effective amount" is intended to include an amount of a combination of compounds claimed effective to treat thrombosis in a mammal. The combination of compounds is preferably a synergistic combination. Synergy, as described for example by Chou and Talalay, Adv. Enzyme Regul. 22:27–55 (1984), occurs when the effect (in this case, an antithrombotic effect) of the compounds when administered in combination is greater than the additive effect of the compounds when administered alone as a single agent. In general, a synergistic effect is most clearly demonstrated at sub-therapeutic amounts of one or more of the combined compounds. Synergy can be in terms of anti-thrombotic effect, anti-cancer effect, improved safety profiles or some other non-additive beneficial effect of the combination compared with the individual components in the same formulation.

By "administered in combination", "combination", or "combined" when referring to compounds described herein, it is meant that the compounds or components are administered together to the mammal being treated. By "sub-therapeutic amount," it is meant that each component when administered to a mammal alone does not give the desired therapeutic effect for the disease being treated but when combined a full therapeutic benefits are achieved.

Dosage and Formulation

Combinations of GPIIb/IIIa antagonist (A) with anticoagulant (B), which might include the following: UFH or low molecular weight heparin (LMWH)or ultra LMWH, pentasaccharide or direct anti-Xa or direct anti-IIa (thrombin) or tissue factor pathway inhibitor (TFPI) are administered for the prevention and treatment of thrombosis and cancer by any means that produces contact of the agents with their site of action.

Dosage forms of compositions suitable for administration contain from about 1 mg to about 100 mg of active ingredient per unit. In these pharmaceutical compositions the active ingredient (combination of GPIIb/IIIa antagonist, A and anticoagulant, B) will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in Remington's Pharmaceutical Sciences, 17th ed., Mack Publishing Company, Easton, Pa., 1985, a standard reference text in this field, the contents of which are incorporated herein by reference.

Useful pharmaceutical dosage-forms for administration of the compounds of this invention can be illustrated as follows:

Capsules:

A large number of unit capsules can be prepared by filling standard two-piece hard gelatin capsules each with 0.1 to 100 mg of active ingredient (GPIIb/IIIa antagonist, A and anticoagulant, B) 150 mg of lactose, 50 mg of cellulose, and 6 mg magnesium stearic. Additionally, other oral delivery enhancer might be added to improve the pharmacokinetics.

Soft Gelatin Capsules:

A mixture of active ingredient (GPIIb/IIIa antagonist, A and anticoagulant, B) in a digestible oil such as soybean oil, cottonseed oil or olive oil can be prepared and injected by means of a positive displacement pump into gelatin to form soft gelatin capsules containing 0.1 to 100 mg of the active ingredient. The capsules should then be washed and dried. Additionally, other oral delivery enhancer might be added to improve the pharmacokinetics.

Tablets:

A large number of tablets can be prepared by conventional procedures so that the dosage unit is 0.1 to 100 mg of active ingredient (GPIIb/IIIa antagonist, A and anticoagulant, B), 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption. Additionally, other oral delivery enhancer might be added to improve the pharmacokinetics.

Suspension:

An aqueous suspension can be prepared for oral administration so that each 5 mL contain 0.1 to 100 mg of finely divided active ingredient (GPIIb/IIIa antagonist, A and anticoagulant, B), 200 mg of sodium carboxymethyl cellulose, 5 mg of sodium benzoate, 1.0 g of sorbitol solution, U.S.P., and 0.025 mg of vanillin. Additionally, other oral delivery enhancer might be added to improve the pharmacokinetics.

Injectable:

A parenteral composition suitable for administration by injection can be prepared by stirring 0.1 to 100 mg by weight of active ingredient (GPIIb/IIIa antagonist, A and anticoagulant, B) as lypholized or soluble formulation. The solution is sterilized by commonly used techniques. The GPIIb/IIIa antagonist, A and the anticoagulant, B would be in the same vial or ampule either in contact or separated by specific coating or by using a physical membrane barrier to be removed upon administration of the combination.

The Formulation Might Include the Following:

Citric acid, anhydrous sodium citrate, mannose, lactose, sodium hydroxide, acid, polycationic carbohydrate such as Chitosan, sodium Caproate, GPIIb/IIIa antagonist (A) and anticoagulant (B). The combined formulation might contain natural antioxidants.

The combined compounds (A and B) of this invention may be formulated such that, although the active ingredients are combined in a single dosage unit, the physical contact between the active ingredients is minimized by the presence of polycationic carbohydrate. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for combined compounds wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of combined compounds in which the one compound is coated with a sustained and/or enteric release polymer, and the other compound is also coated with a polymer such as a low viscosity grade of hydroxypropyl methylcellulose or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric-coated compound and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the combined compounds, whether administered in a single dosage form or administered in separate forms but at the same time or concurrently by the same manner, will be readily apparent to those skilled in the art, based on the present disclosure.

Combination:

Each therapeutic compound (GPIIb/IIIa antagonist, A and anticoagulant, B) of this invention can be in any dosage form, such as those described above, and can also be administered in various ways, as described above. For example, the compounds may be formulated together (that is, combined together in one capsule, tablet, powder, or liquid, etc.) as a combination product.

Preferably, the route of administration of therapeutic combinations herein is intravenously, subcutaneously or orally.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of a GPIIb/IIIa antagonist (A) and anticoagulant (B) including either UFH, LMWH, ultra-LMWH, pentasaccharide, direct anti-Xa, anti-IIa, or TFPI combination is readily ascertainable by a medical practitioner skilled in the art, based upon the present disclosure. By way of general guidance, typically a daily dosage may be about 1 to 100 milligram of each component. By way of general guidance, when the compounds are administered in combination, the dosage amount of each component or the anticoagulant may be reduced. This reduced amount could be by about 20–80% relative to the usual dosage of the component when it is administered alone as a single agent for the treatment of thrombosis and cancer, in view of the synergistic effect of the combination.

Obviously, numerous modifications and variations of the present invention are possible in light of the above teachings. It is therefore to be understood that within the scope of the appended claims, the invention may be practiced otherwise than as specifically described herein.

EXAMPLES

Example 1

The combination of unfractionated heparin (UFH) or LMWH ultra-LMWH, Pentasaccharide or modified heparin and a short acting GPIIb/IIIa antagonists such as Integrilin, tirofiban or DUP728 in the presence of polycationic carbohydrate such Chitosan, citric acid/sodium citrate, mannitol, and other non-active ingredients as described in the different dosage form section at pH 4–6 is a preferred formulation for intravenous administration.

Example 2

The combination of UFH or LMWH, ultra-LMWH, Pentasaccharide or modified heparin and a long acting GPIIb/IIIa antagonists such as XV454, XV459 or other long acting GPIIb/IIIa antagonists in the presence of polycationic carbohydrate such Chitosan, citric acid/sodium citrate, mannitol and other non-active ingredients as described in the different dosage form section at pH 4–6 is a preferred formulation for intravenous and subcutaneous administration.

Example 3

The combination of other anticoagulants including small molecule anti-Xa, anti-IX/IXa, anti-IIa or r-TFPI and a short acting GPIIb/IIIa antagonists such as Integrilin, tirofiban or DUP728 in the presence of citric acid/sodium citrate, mannitol, and other non-active ingredients as described in the different dosage form section at pH 4–6 is a preferred formulation for intravenous administration.

Example 4

The combination of other anticoagulants including small molecule anti-Xa, anti-IX/IXa, anti-IIa or r-TFPI and a long acting GPIIb/IIIa antagonists such as XV454, XV459 or other long acting GPIIb/IIIa antagonists in the presence of polycationic carbohydrate such Chitosan, citric acid/sodium citrate, mannitol at pH 4–6 is a preferred formulation for intravenous, subcutaneous, oral, transdermal, intranasal or any other delivery mode of administration.

TABLE 1

Tumor Type Associated with Venous Thrombosis

Pancreatic tumors
Mucin-secreting adenocarcinoma from the gastrointestinal system
Lung carcinoma
Ovarian carcinoma
Endometrial carcinoma
Intracranial cancers
Acute promyelocytic leukemia
Myeloproliferative disorders
Breast Cancer

TABLE 2

| Disease | Prevalence (or Incidence*) |
|---|---|
| Solid tumor cancer | >600,000* |
| Lung, breast, prostrate, colon, renal bladder, pancreatic, gioblastomas, Neuroblastomas and others | |
| Ocular Ailments | |
| Macular degeneration | 650,000 |
| Diabetic retinopathy | 300,000 |
| Corneal transplant | 100,000 |
| Myopic degeneration | 200,000 |

TABLE 2-continued

| Disease | Prevalence (or Incidence*) |
|---|---|
| Inflammatory Diseases | |
| Arthritis | 2.1 million |
| Psoriasis | 3.0 million |
| IBD/other chronic IDs | >2.0 million |

*New cases per year

What claimed is:

1. A method, comprising treating tumor growth and metastasis in a mammal, said treating including administering a composition to the mammal, said composition comprising a sub-therapeutic dose of a GPIIb/IIIa antagonist, a sub-therapeutic dose of an anticoagulant, and a polycationic carbohydrate, wherein the anticoagulant comprises unfractionated heparin (UFH), low molecular weight heparin (LMWH), ultra LMWH, or pentasaccharide.

2. The method of claim 1, wherein the LMWH is selected from the group consisting of tinzaparin, certoparin, parnaparin, nadroparin, ardeparin, enoxaparin, reviparin, reviparin, dalteparin, and fraxiparin.

3. The method or claim 1, wherein the GPIIb/IIIa antagonist is selected from the group consisting of Abciximab, XV459), DMP754 (Roxifiban), DMP802, and XV454.

4. The method of claim 1, wherein the anticoagulant comprises direct anti-Xa.

5. The method of claim 1, wherein the anticoagulant comprises anti-IX/Xa.

6. The method of claim 1, wherein the anticoagulant comprises direct anti-IIa (thrombin).

7. The method of claim 1, wherein the anticoagulant comprises direct anti-VIIa.

8. The method of claim 1, wherein the anticoagulant comprises anti-tissue factor.

9. The method of claim 1, wherein the mammal is a human cancer patient.

10. A method, comprising treating tumor growth and metastasis in a mammal, said treating including administering a composition to the mammal, said composition comprising a sub-therapeutic dose of a GPIIb/IIIa antagonist, a sub-therapeutic dose of an anticoagulant, and a polycationic peptide, wherein the anticoagulant comprises unfractionated heparin (UFH), low molecular weight heparin (LMWH, ultra LMWH, or pentasaccharide.

11. The method of claim 10, wherein the GPIIb/IIIa antagonist is selected from the group consisting pf Abciximab, XV459, DMP754 (Roxifiban), DMP802, and XV454.

12. The method of claim 10, wherein the anticoagulant comprises direct anti-Xa.

13. The method of claim 10, wherein the anticoagulant comprises anti-IX/IXa.

14. The method of claim 10, wherein the anticoagulant comprises direct anti-IIa (thrombin).

15. The method of claim 10, wherein the anticoagulant comprises anti-VIIa.

16. The method of claim 10, wherein the anticoagulant comprises anti-tissue factor.

17. The method of claim 10, wherein the mammal is a human cancer patient.

* * * * *